United States Patent [19]
Liang et al.

[11] Patent Number: 5,475,151
[45] Date of Patent: Dec. 12, 1995

[54] PROCESS FOR THE PREPARATOIN OF CYCLOPROPYLMETHANOL

[76] Inventors: Shaowo Liang, 2705 Berkshire La., Kingsport, Tenn. 37660; Timothy W. Price, 506 Birch St., Church Hill, Tenn. 37642

[21] Appl. No.: 345,193

[22] Filed: Nov. 28, 1994

[51] Int. Cl.$^6$ ............................ C07C 35/04; C07C 35/02
[52] U.S. Cl. ............................ 568/700; 568/839
[58] Field of Search ................... 568/700, 839, 568/838

[56] References Cited

U.S. PATENT DOCUMENTS

| | | | |
|---|---|---|---|
| 3,959,324 | 5/1976 | Peterson et al. | 568/700 |
| 4,065,480 | 12/1977 | Peterson et al. | 568/700 |
| 5,128,488 | 7/1992 | Mortreux et al. | 568/700 |
| 5,220,020 | 6/1993 | Buchwald et al. | 568/700 |
| 5,371,270 | 12/1994 | Kaufhold et al. | 568/700 |

*Primary Examiner*—Werren B. Lone
*Attorney, Agent, or Firm*—J. Frederick Thomsen; Harry J. Gwinnell

[57] ABSTRACT

Disclosed is a process for the preparation of cyclopropylmethanol(hydroxymethylcyclopropane) by the hydrogenation of cyclopropanecarboxaldehyde in the presence of a cobalt or nickel catalyst.

4 Claims, No Drawings

PROCESS FOR THE PREPARATOIN OF CYCLOPROPYLMETHANOL

This invention pertains to a process for the preparation of cyclopropylmethanol (hydroxymethylcyclopropane). More specifically, this invention pertains to the production of cyclopropylmethanol by the hydrogenation of cyclopropanecarboxaldehyde.

Cyclopropylmethanol is useful as an intermediate for the synthesis of various organic chemicals such as, for example, pesticides, fungicides, herbicides and insecticides as disclosed in U.S. Pat. Nos. 3,959,324, 3,998,889 and 4,065,480. Cyclopropylmethanol has been prepared from cyclopropanecarboxylic acid by reduction with lithium aluminum hydride (U.S. Pat. No. 3,454,575); by the reaction of organometallic compounds such as 3-butenyltributyltin in the presence of electrophilic compounds (U.S. Pat. Nos. 4,085,273, 4,065,480, 3,998,889 and 3,959,324); and by the palladium-catalyzed cyclopropanation of allyl alcohol with diazomethane [Mendeleev Commun., 1 pp. 13–15 (1992) and Izv. Akad. Nauk SSSR, Ser. Khim., 12, pp. 2752–2755 (1989)]. These processes involve costly materials and present serious safety problems in materials handling.

German Patent DE 3,538,132 describes the preparation of cyclopropylmethanol by the hydrogenation of cyclopropanecarboxylic acid esters in the presence of a zinc chromite catalyst. This process requires high pressures (200–300 bar) and high temperatures (200°–320° C.) which requires high pressure hydrogenation vessels.

The process of the present invention provides a economical means for the production of cyclopropylmethanol which avoids the necessity of using expensive reagents which are difficult to handle and is carried out under mild conditions. The process comprises the hydrogenation of cyclopropanecarboxaldehyde in the presence of a cobalt or nickel catalyst under hydrogenation conditions of pressure and temperature to produce cyclopropylmethanol. An important feature of the process of this invention is that hydrogenation virtually stops after formation of the cyclopropylmethanol. The selectivity of the conversion of cyclopropanecarboxaldehyde to cyclopropylmethanol normally is in the range of 93–100%.

Examples of the cobalt and nickel catalysts which may be employed in the process include Raney cobalt, Raney nickel and supported nickel catalysts. The support material of the supported nickel catalysts may be selected from a wide variety of known catalyst support materials such as, for example, carbon, alumina, silica, silica-alumina, titania, kieselguhr, molecular sieves, zeolites, and the like. The nickel catalysts may contain minor amounts of modifiers and/or promoters such as, for example, molybdenum, chromium, iron, zirconium, and/or cobalt. The supported nickel catalysts comprise from about 20 to 70, preferably from 40 to 60 weight percent, nickel. Raney cobalt, Raney nickel and 40 to 60 weight percent nickel on an alumina support constitute the preferred hydrogenation catalysts.

The hydrogenation conditions of temperature and pressure useful in carrying out the process of this invention can vary substantially depending on several factors such as contact time with the cobalt or nickel catalyst, the amount of catalyst and the choice of solvent. Hydrogenation temperatures of about 10° to 150° C. may be used although milder temperatures in the range of about 20° to 80° C. are advantageous to maximize conversion to the desired cyclopropylmethanol and minimize the reduction of the cyclopropane ring. The hydrogenation process may be carried out using total pressures in the range of about 1 to 414.5 bars absolute, preferably about 1.4 to 70 bars absolute, and more preferably 3 to 8 bars absolute. As noted above, the optimum combination of temperature and pressure depends on other process variables but can be readily ascertained by those skilled in the art.

The process of this invention may be carried out in the presence of an inert solvent. Examples of such solvents include water, aliphatic and aromatic hydrocarbons such as cyclohexane, heptane, toluene, xylene and mixed xylene isomers, ethers such as tetrahydrofuran, alcohols such as methanol, ethanol and n-butanol or the reaction product, i.e., cyclopropylmethanol).

A particularly preferred embodiment of the present invention involves the preparation of cyclopropylmethanol by the hydrogenation of cyclopropanecarboxaldehyde at a temperature of about 20° to 50° C. and a pressure of about 2.4 to 5.2 bars absolute in the presence of a catalyst selected from Raney cobalt, Raney nickel and supported nickel catalysts and, optionally, an inert solvent selected from heptane and cyclohexane. This embodiment of the invention usually gives selectivities of 97–100%. The use of higher temperatures and more polar solvents generally results in an increase in the amount of n-butanol formed due to hydrogenation of the cyclopropane ring to form n-butanal which was further reduced to form n-butanol.

The preferred conditions about 20° to 50° C. and about 2.4 to 5.2 bars absolute can be handled conveniently in general purpose, glass-lined plant equipment. The process of this invention preferably is carried out in the absence of solvent, which has significant advantage in the production rate of the process. High purity cyclopropanecarboxaldehyde is not required for the hydrogenation. For example, cyclopropanecarboxaldehyde containing 5–15% of crotonaldehyde typically is obtained in the preparation of cyclopropanecarboxaldehyde by the thermal isomerization of 2,3-dihydrofuran. When such cyclopropanecarboxaldehyde/crotonaldehyde mixtures are hydrogenated, crotonaldehyde is completely reduced to n-butanol. Pure cyclopropylmethanol can be obtained by distillation after the removal of the cobalt or nickel catalyst.

The process may be carried out in a batch, semi-continuous or continuous mode of operation. For example, batch operation may comprise agitating a slurry of a cobalt or nickel catalyst in cyclopropanecarboxaldehyde and, optionally, a solvent in a pressure vessel for a time sufficient to hydrogenate essentially all of the cyclopropanecarboxaldehyde to cyclopropylmethanol. The catalyst can be separated from the hydrogenated mixture by filtration and the components of the filtrate separated by distillation.

A preferred mode of operation uses a fixed bed of a cobalt or nickel catalyst wherein cyclopropanecarboxaldehyde is hydrogenated in the gas or, especially, liquid phase, optionally in the presence of an inert diluent or solvent. Liquid phase operation typically involves feeding a solution of cyclopropanecarboxaldehyde in an inert solvent-diluent to the top of a columnar pressure reactor containing one or more fixed beds of a cobalt or nickel catalyst. The reactant solution flows (trickles) over the catalyst bed in the presence of hydrogen at elevated temperature and pressure and the hydrogenated product exits the bottom of the reactor and is separated into its components by distillation.

The process provided by the present invention is further illustrated by the following examples. Gas chromatographic (GC) analyses were performed on a Hewlett-Packard 5890 series II gas chromatography with a 30 meter DB-Wax and a 30 meter DB-17 capillary columns. The identities of the products obtained were confirmed by nuclear magnetic

EXAMPLE 1

To a 250-ml pressure bottle was charged 2.5 g of water-wet Raney-nickel. The catalyst was rinsed 3 times with distilled water, then 3 times with ethanol. To the catalyst was added ethanol (20 ml) followed by 5 g of cyclopropanecarboxaldehyde (93% assay, containing 7% crotonaldehyde). The bottle was placed in a Parr shaker type hydrogenation apparatus and purged with nitrogen, then with hydrogen. The bottle was pressurized to 4.45 bar absolute with hydrogen and agitation begun. The mixture was maintained at 25°–28° C. throughout the reaction period. After 16 hours, the catalyst was removed by filtration. GC analysis of the crude mixture showed (disregarding solvent): 89.58% cyclopropylmethanol and 10.42% n-butanol. The selectivity of cyclopropanecarboxaldehyde to cyclopropylmethanol was 96.4%.

EXAMPLE 2

To a 250-ml pressure bottle was charged 2 g of water-wet Raney-nickel. The catalyst was rinsed 3 times with distilled water, 3 times with tetrahydrofuran and then 3 times with cyclohexane. To the catalyst was added cyclohexane (20 ml) followed by 5 g of cyclopropanecarboxaldehyde (91.63% assay, containing 8.73% crotonaldehyde). The bottle was placed in a Parr shaker type hydrogenation apparatus and purged with nitrogen then with hydrogen. The bottle was pressurized to 4.72 bar absolute with hydrogen and agitation begun. The mixture was maintained at 25°–28° C. throughout the reaction period. After 7 hours, the catalyst was removed by filtration. GC analysis of the crude mixture showed (disregarding solvent): 89.28% cyclopropylmethanol and 10.72% n-butanol. The selectivity of cyclopropanecarboxaldehyde to cyclopropylmethanol was 97.4%.

EXAMPLE 3

To a 250-ml pressure bottle was charged 2 g of water-wet Raney-nickel. The catalyst was rinsed 3 times with distilled water, 3 times with tetrahydrofuran and then 3 times with heptane. To the catalyst was added heptane (20 ml) followed by 5 g of cyclopropanecarboxaldehyde (92% assay, containing 8% crotonaldehyde). The bottle was placed in a Parr shaker type hydrogenation apparatus and purged with nitrogen then with hydrogen. The bottle was pressurized to 4.45 bar absolute with hydrogen and agitation begun. The mixture was maintained at 25°–28° C. throughout the reaction period. After 16 hours, the catalyst was removed by filtration. GC analysis of the crude mixture showed (disregarding solvent): 90.18% cyclopropylmethanol and 9.82% n-butanol. The selectivity of cyclopropanecarboxaldehyde to cyclopropylmethanol was 98.0%.

EXAMPLE 4

To a 250-ml pressure bottle was charged 4 g of water-wet Raney-nickel. The catalyst was rinsed 3 times with distilled water then 3 times with tetrahydrofuran. To the catalyst was added 10 g of cyclopropanecarboxaldehyde (91.63% assay, containing 8.73% crotonaldehyde). The bottle was placed in a Parr shaker type hydrogenation apparatus and purged with nitrogen, then with hydrogen. The bottle was pressurized to 4.72 bar absolute with hydrogen and agitation begun. The mixture was maintained at 25°–28° C. throughout the reaction period. After 4.5 hours, the catalyst was removed by filtration. GC analysis of the crude mixture showed (disregarding solvent): 85.62% cyclopropylmethanol and 14.38% n-butanol. The selectivity of cyclopropanecarboxaldehyde to cyclopropylmethanol was 93.4%.

EXAMPLE 5

To a 250-ml pressure bottle was charged 2 g of water-wet Raney-nickel. The catalyst was rinsed 3 times with distilled water, then 3 times with tetrahydrofuran. To the catalyst was added 20 ml of tetrahydrofuran followed by 5 g of cyclopropanecarboxaldehyde (91.63% assay, containing 8.73% crotonaldehyde). The bottle was placed in a Parr shaker type hydrogenation apparatus and purged with nitrogen then with hydrogen. The bottle was pressurized to 4.72 bar absolute with hydrogen and agitation begun. The mixture was maintained at 25°–28° C. throughout the reaction period. After 16 hours, the catalyst was removed by filtration. GC analysis of the crude mixture showed (disregarding solvent): 87.27% cyclopropylmethanol and 12.73% n-butanol. The selectivity of cyclopropanecarboxaldehyde to cyclopropylmethanol was 95.2%.

EXAMPLE 6

This example shows that no further reduction of the cyclopropylmethanol product occurs after its formation.

To a 250-ml pressure bottle was charged 1 g of water-wet Raney-nickel. The catalyst was rinsed 3 times with distilled water, 3 times with tetrahydrofuran and then 3 times with cyclohexane. To the catalyst was added 10 ml of cyclohexane followed by 2.5 g of cyclopropylmethanol. The bottle was placed in a Parr shaker type hydrogenation apparatus and purged with nitrogen then with hydrogen. The bottle was pressurized to 4.72 bar absolute with hydrogen and agitation begun. The mixture was maintained at 25°–28° C. throughout the reaction period. After 16 hours, the catalyst was removed by filtration. GC analysis of the crude mixture failed to detect any n-butanol and, therefore, none of the cyclopropyl ring had been hydrogenated.

EXAMPLE 7

To a 250-mL pressure bottle was charged 2 g of Raney-cobalt. The catalyst was rinsed 3 times with tetrahydrofuran and then 3 times with cyclohexane. To the catalyst was added cyclohexane (20 mL) followed by 5 g of cyclopropanecarboxaldehyde (90.80% assay, containing 8.31% crotonaldehyde). The bottle was placed in a Parr shaker type hydrogenation apparatus and purged with nitrogen then with hydrogen. The bottle was pressurized to 4.67 bar absolute with hydrogen and agitation begun. The mixture was maintained at 25°–29° C. throughout the reaction period. After 16 hours, the catalyst was removed by filtration. GC analysis of the crude mixture showed (disregarding solvent): 90.58% cyclopropylmethanol and 7.93% n-butanol. The selectivity was greater than 99%.

EXAMPLE 8

To a 250-mL pressure bottle was charged 1 g of Raney-cobalt and 20 g of cyclopropanecarboxaldehyde (96.95% assay, containing 0.15% butyraldehyde). The bottle was placed in a Parr shaker type hydrogenation apparatus and purged with nitrogen then with hydrogen. The bottle was pressurized to 4.45 bar absolute with hydrogen and agitation begun. The mixture was maintained at 40° C. over a reaction period of 20 hours. GC analysis of the crude reaction spectrometry and gas chromatography-mass spectrometry by comparison to authentic samples purchased from Aldrich.

mixture showed 19.80 g (275 mmol, 99.3% yield) of cyclopropylmethanol and 0.09 g (1.2 mmol) of n-butanol were obtained. The selectivity was greater than 99%. Distillation of the crude product gave cyclopropylmethanol with 99% purity.

EXAMPLE 9

To a 500-ml pressure bottle was charged 10 g of Raney-cobalt and 200 g of cyclopropanecarboxaldehyde (90.46% assay containing 7.97% crotonaldehyde). The bottle was placed in a Parr shaker type hydrogenation apparatus and purged with nitrogen, then with hydrogen. The bottle was pressurized to 4.80 bar absolute with hydrogen and agitation begun. The mixture was maintained at 25°–28° C. throughout the reaction period. After 40 hours, no further hydrogen uptake was observed and the reaction mixture (203 g, excluding catalyst) was obtained. GC analysis of the reaction mixture showed 185.44 g (2.576 mol, 99.7% yield) of cyclopropylmethanol and 16.36 g (0.227 mol) n-butanol. The selectivity was 100%. Distillation of the crude product gave cyclopropylmethanol having a purity of 99.7%.

EXAMPLE 10

To a 300-mL autoclave equipped with a catalyst basket, containing 15 g of a supported catalyst consisting of 57 weight percent nickel on an alumina support, and an overhead stirrer was placed 120 g of cyclohexane. The catalyst was pretreated with hydrogen at 200° C. and 14.80 bar absolute for 2 hours in the autoclave. After cooling to 20° C. and reducing the pressure to 4.45 bar absolute, cyclopropanecarboxaldehyde 30 g, (91.90% assay, containing 8.10% crotonaldehyde) was introduced via a blow case under hydrogen. The mixture was stirred at 20° C. and 4.45 bar absolute hydrogen for 24 hours. After the removal of catalyst, GC analysis of the crude mixture showed (disregarding solvent): 88.56% cyclopropylmethanol and 11.25% n-butanol. The selectivity was 96.4%.

EXAMPLE 11

To a 300-mL autoclave equipped with a catalyst basket, containing 15 g of a supported catalyst consisting of 43 weight percent nickel on an alumina support, and an overhead stirrer was placed 120 g of cyclohexane. The catalyst was pretreated with hydrogen at 200° C. and 14.80 bar absolute for 2 hours in the autoclave. After cooling to 30° C. and reducing the pressure to 4.45 bar absolute, cyclopropanecarboxaldehyde (30 g 91.90% assay, containing 8.10% crotonaldehyde) was introduced via a blow case under hydrogen. The mixture was stirred at 30° C. and 4.45 bar absolute hydrogen for 24 hours. After the removal of catalyst, GC analysis of the crude mixture showed (disregarding solvent): 25.85% cyclopropanecarboxaldehyde, 65.28% cyclopropylmethanol, 7.90% n-butanol and 0.96% n-butanal. The selectivity was greater than 99% with 71.9% conversion of cyclopropanecarboxaldehyde.

COMPARATIVE EXAMPLE 1

To a 250-ml pressure bottle were charged 0.5 g of 5% palladium on carbon catalyst followed by 5 g of cyclopropanecarboxaldehyde (93% assay, containing 7% crotonaldehyde) and 20 ml of ethyl acetate. The bottle was placed in a Parr shaker type hydrogenation apparatus and purged with nitrogen then with hydrogen. The bottle was pressurized to 4.72 bar absolute with hydrogen and agitation begun. The mixture was maintained at 50° C. throughout the reaction period. After 19 hours, the catalyst was removed by filtration. GC analysis of the crude mixture showed (disregarding solvent): 40.68% unreacted cyclopropanecarboxaldehyde and 59.32% n-butanol. Cyclopropylmethanol was not detected.

COMPARATIVE EXAMPLE 2

To a glass liner with a magnetic stirrer were charged 0.7 g of 5% palladium on carbon catalyst and 7 g of cyclopropanecarboxaldehyde (94% assay, containing 6% crotonaldehyde). The glass liner was placed in a 250 ml autoclave and purged with nitrogen then with hydrogen. The autoclave was pressurized to 42.4 bar absolute with hydrogen and heated to 60° C. The mixture was stirred under these conditions for 16 hours. The reactor was cooled and vented with nitrogen and the catalyst was removed by filtration. GC analysis of the crude mixture showed that n-butanol was the only product obtained (100% over reduction of cyclopropanecarboxaldehyde and crotonaldehyde). Cyclopropylmethanol was not detected.

The invention has been described in detail with particular reference to preferred embodiments thereof, but it will be understood that variations and modifications can be effected within the spirit and scope of the invention.

We claim:

1. Process for the preparation of cyclopropylmethanol which comprises hydrogenating cyclopropanecarboxaldehyde with hydrogen in the presence of a cobalt or nickel hydrogenation catalyst under hydrogenation conditions of pressure and temperature.

2. Process according to claim 1 wherein the hydrogenation catalyst is selected from Raney cobalt, Raney nickel and supported nickel catalysts.

3. Process for the preparation of cyclopropylmethanol which comprises hydrogenating cyclopropanecarboxaldehyde with hydrogen in the presence of a hydrogenation catalyst selected from Raney cobalt, Raney nickel and supported nickel catalysts comprising 40 to 60 weight percent nickel on an alumina support at a pressure of about 3 to 8 bar absolute and a temperature of about 20° to 80° C.

4. Process for the preparation of cyclopropylmethanol which comprises hydrogenating cyclopropanecarboxaldehyde with hydrogen at a temperature of about 20° to 50° C. and a pressure of about 2.4 to 5.2 bar absolute in the presence of a hydrogenation catalyst selected from Raney cobalt, Raney nickel and supported nickel catalysts comprising 40 to 60 weight percent nickel on an alumina support.

* * * * *